United States Patent [19]

Tschunt

[11] 4,203,036
[45] May 13, 1980

[54] X-RAY DIAGNOSTIC APPARATUS FOR PRODUCING TRANSVERSE LAYER IMAGES

[75] Inventor: Edgar Tschunt, Rathsberg, Fed. Rep. of Germany

[73] Assignee: Siemens Aktiengesellschaft, Berlin & Munich, Fed. Rep. of Germany

[21] Appl. No.: 817,209

[22] Filed: Jul. 20, 1977

[30] Foreign Application Priority Data

Nov. 2, 1976 [DE] Fed. Rep. of Germany ....... 2650237

[51] Int. Cl.² ............................................. G01N 23/00
[52] U.S. Cl. .................................. 250/445 T; 250/505
[58] Field of Search .................... 250/445 T, 404, 505, 250/385, 363, 407

[56] References Cited

U.S. PATENT DOCUMENTS

| 3,250,916 | 5/1966 | Rogers | 250/404 |
| 3,778,614 | 12/1973 | Hounsfield | 250/445 T |
| 4,031,395 | 6/1977 | Lemay | 250/445 T |
| 4,047,041 | 9/1977 | Houston | 250/445 T |
| 4,052,618 | 10/1977 | Hounsfield | 250/445 T |

OTHER PUBLICATIONS

"Computerized Tomographic Scanner," *American Science and Engineering, Inc.*, Pub. No. ASE-3869, Apr. 1976.

*Primary Examiner*—Bruce C. Anderson
*Attorney, Agent, or Firm*—Hill, Van Santen, Steadman, Chiara & Simpson

[57] ABSTRACT

In an illustrated embodiment, a ring-shaped X-ray source is operative to supply a fan-shaped X-ray beam from an incremental region thereof, successive incremental regions being sequentially activated to change the angular relationship between the beam and the subject. By way of example, three incremental regions equally spaced about the source ring may be simultaneously activated and then shifted in synchronism with the rotation of a collimator ring such that openings in the collimator ring are continually aligned with the active source regions, and collimator blades are continuously aligned with the active source regions so as to supply transmitted rays from each source region to a series of stationary detector elements. In the illustrated embodiment, the X-ray source regions and a detector ring are laterally offset from each other, and a diaphragm arrangement directs each beam at a slight angle so as to laterally bypass the adjacent portion of the detector ring while impinging on the receiving detectors. Motion of the collimator ring may be utilized to control shifting of the X-ray beams, so that such shifting is precisely synchronized with the movement of the collimator ring.

10 Claims, 4 Drawing Figures

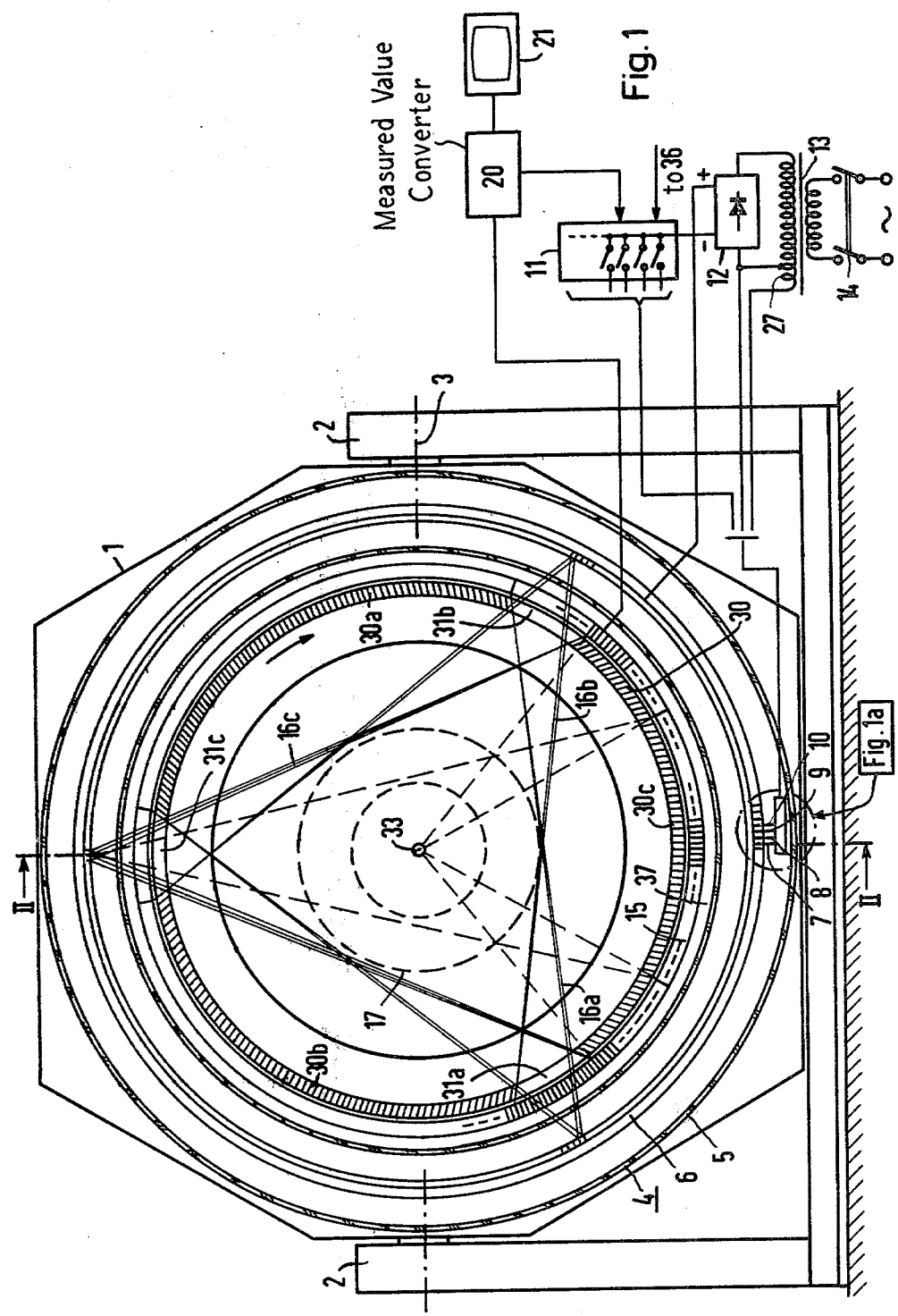

X-RAY DIAGNOSTIC APPARATUS FOR PRODUCING TRANSVERSE LAYER IMAGES

BACKGROUND OF THE INVENTION

This invention relates to an X-ray diagnostic apparatus for producing transverse layer images of a subject, comprising an X-ray measuring arrangement including an X-ray source for generating a fan-shaped X-ray beam which penetrates the subject and of which the cross-section perpendicularly of the layer plane is equal to the layer thickness and, in the layer plane, is so great that the entire subject is penetrated, and a radiation receiver which determines the intensity of radiation behind the subject, which is in the form of a circular ring into which the subject can be introduced and has a series of detectors, and further comprising means for changing the direction of the axis of symmetry of the X-ray beam and comprising a computer for transforming the signals supplied by the radiation receiver into a layer image.

U.S. Pat. No. 3,778,614 describes an X-ray diagnostic apparatus which embodies all these features except for the circular radiation receiver. In this known X-ray diagnostic apparatus, the radiation receiver is laterally displaceable. When the subject is scanned, lateral displacements and rotational movements through a predetermined angle, for example one degree, follow one another in an alternating sequence until the entire subject has been scanned. The transducer includes a computer which calculates the transverse layer image from the measured absorption values. One disadvantage of this X-ray diagnostic apparatus is that the time required to form an image is relatively long on account of the necessary mechanical movement of the radiation detector and the X-ray tube.

An X-ray diagnostic apparatus of the kind referred to above is described in the publication entitled "Computerized Tomographic Scanner" of American Science and Engineering, Inc., Publication No. ASE-3869 April 1976. This X-ray diagnostic apparatus comprises a circular radiation receiver which surrounds the subject to be examined. Accordingly, it is only necessary to rotate the X-ray source, i.e. the radiation receiver does not have to be moved. Consequently, the time required to form an image is reduced in relation to the apparatus known from U.S. Pat. No. 3,778,614. Moreover, a simpler mechanical structure is also obtained.

SUMMARY OF THE INVENTION

The object of the present invention is to further improve an X-ray diagnostic apparatus of the kind referred to above in regard to the time required to form an image. More particularly, the object of the invention is to provide an apparatus of this type in which there is no longer any need for the measuring arrangement to be mechanically moved.

According to the invention, this object is achieved in that the X-ray source manifests an annular anode arrangement which surrounds the radiation receiver, in that a number of cathodes dependent upon the desired number of measured values is arranged opposite the anode arrangement, in that means are provided for switching on the electron beam in steps between at least one cathode and the anode, and in that the anode arrangement and the radiation receiver are disposed in such a way that the X-ray beam initially passes laterally by the radiation receiver in the radiation direction and then impinges thereon. In the X-ray diagnostic apparatus according to the invention, the X-ray beam is rotated purely electronically by successively releasing the electron radiation in steps between a cathode, respectively, and the anode. There is no longer any need for the X-ray source or the radiation receiver to be mechanically rotated. In addition to the simple mechanical structure of the apparatus, the time taken to form an image is extremely short.

Other objects, features and advantages of the invention will be apparent from the following description of an illustrative embodiment taken in connection with the accompanying sheets of drawings.

BRIEF DESCRIPTION OF THE DRAWINGS

FIG. 1 is a somewhat diagrammatic cross sectional view illustrating an X-ray diagnostic apparatus according to the present invention;

DETAILED DESCRIPTION

Figure 1A:
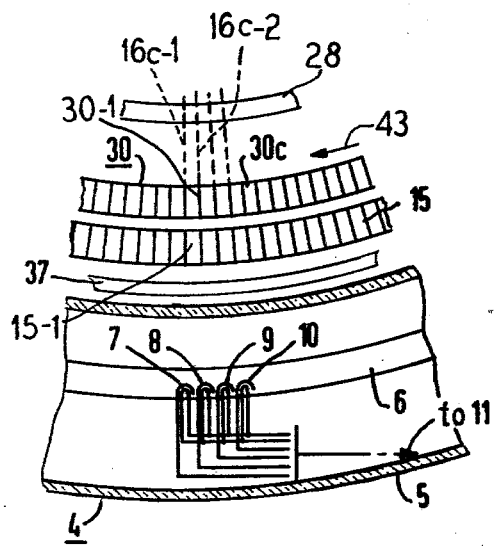
FIG. 1a is a somewhat diagrammatic partial enlarged view of the portion of the apparatus of FIG. 1 indicated by the dot dash circle at the lower central portion of FIG. 1.

The apparatus illustrated in the drawing comprises a housing 1 which is mounted on two supports 2 so as to be angularly adjustable about a horizontal axis 3. By rotating the housing 1 about the axis 3, it is possible to select the position of the required transverse layer of the subject under examination. Arranged in the housing 1 is an X-ray source 4 which has an evacuated tubular envelope of glass forming a ring 5 in which an anode 6, also in the form of a ring, is arranged. A number of cathodes 7, 8, 9, 10, etc. is associated with the anode 6. The cathodes 7, etc. are connected to a switching device 11 which connects the negative terminal of a high-voltage rectifier 12 fed by a high-voltage transformer 13 in steps to the cathodes 7, etc. The positive terminal of the high-voltage rectifier 12 is connected to the anode 6. The primary winding of the high-voltage transformer 13 is connectible to the mains through a master switch 14. The X-ray source 4 concentrically surrounds a radiation receiver 15 which is also in the form of a circular ring and which consists of a series of individual detectors of which the number is dependent upon the desired number of measured values. The number of cathodes 7, etc. is also dependent upon the number of measured values. For example, the number of cathodes may be selected in such a way that the X-ray beam 16a, b, c, emitted by the anode is rotated in steps through angles of one degree (1°).

The switching device 11 is designed in such a way that several, namely three, X-ray beams 16a, 16b and 16c simultaneously penetrate the patient from different directions and move (or migrate) in equal steps in synchronism with one another. The central rays of the X-ray beams 16a, b, c are thus staggered 120°. A collimator 30 is arranged inside the radiation receiver 15, comprising a blade section 30a, b, c for each X-ray beam 16a, b, c. The blades of the blade sections 30a, b, c are aligned to the respective focus so that it is only the radiation emanating from the focus, and not the stray radiation, which is picked up (or detected) by the radiation receiver 15. Openings 31a, b, c are provided between the blade sections 30a, b, c allowing the X-radiation directed at the subject to pass through. The collimator ring 30 is rotatable in synchronism with the activation of the successive sets of three focuses about the center point 33 of the X-ray source 4 by drive means 32, FIG. 2, in the form of an electric motor. The synchronous movement of the collimator ring 30 and the focuses is ensured by the fact that the collimator ring in the form of a circular ring with the openings 31a, b, c is connected to a pulse generator for controlling the switching means 11 for switching on successive sets of three electron beams. This pulse generator is formed by a cylindrical apertured ring 34 with which an opto-electronic transducer 35, 36 is associated.

The radiation receiver 15 is arranged laterally on an annular slit diaphragm 37 which delimits the X-ray beams 16a, b, c perpendicularly of the layer plane and comprises extensions 38, 39 for screening off the X-radiation directed at the subject under examination.

The housing 1 has a central opening 17 into which a couch carrying a patient can be introduced.

The radiation receiver 15 is connected to a measured value converter 20 which calculates an image of the radiation-penetrated transverse layer of the patient from the measured values and reproduces it on a display unit 21.

The X-ray beams 16a, b, c and the radiation receiver 15 are aligned with one another in such a way that, viewed in the direction of radiation, the X-ray beams initially pass laterally by the radiation receiver 15 at the point 22 (FIG. 2) and impinge thereon after they have penetrated the patient.

In order to examine a patient, i.e. to form a layer image, three switches of the switching device 11 are first closed. In this way, high voltage is applied between the anode and three cathodes and the X-ray beams 16a, b, c are emitted, for example, in the directions shown in FIG. 1. After the converter 20 has processed the measured values of the radiation receiver 15, it delivers to the switching device 11 a signal for opening these switches and for closing the following switches. Accordingly, the axis of symmetry of each X-ray beam moves clockwise through another one degree (1°) for example. After the converter 20 has again processed the measured values of the radiation receiver 15, it delivers to the switching device 11 a signal for opening these switches and for closing the following switches. Accordingly, the axis of symmetry of the X-ray beams moves through another one degree (1°). The step-by-step rotation of the X-ray beams is repeated until each X-ray beam has covered a predetermined angular range of, for example, 120°. Formation of the image is then complete and the calculated cross-sectional image can be reproduced on the display unit 21.

It can be seen from FIG. 1 that the X-ray beams 16a, b, c are fan-shaped and, in the layer plane, are so large that the entire patient is simultaneously penetrated by them. The extent (or spread) of the X-ray beams perpendicularly of the layer plane is substantially equal to the layer thickness.

To ensure that an image can be quickly formed in the shortest possible time, all the cathodes 7, etc. are simultaneously heated, i.e. are simultaneously connected to a filament transformer which is part of the high-voltage transformer 13 and which is denoted by the reference 27 in FIG. 1. Accordingly, to switch on the X-radiation at a certain angle, all that is necessary is to connect the high voltage to the corresponding cathode. The X-radiation then appears immediately.

According to the invention, it is also possible to arrange a control grid between each cathode 7, etc. and the anode 6 and to provide a switching device by which, for successive switching on the electron beam, to each control grip can be applied a voltage releasing that beam.

A diaphragm arrangement 28 is provided for delimiting the fan-shaped X-ray beams 16a, b, c.

In the embodiment illustrated, three staggered X-ray beams 16a, b, c are provided so that the subject under examination can be scanned very quickly. This is because one X-ray beam need only move through an angle of about 120°. According to the invention, it is also possible to provide only two or only one X-ray beam. In this case, one X-ray beam has to cover an angle of 180° or 360°. In this case, too, extremely rapid scanning is ensured by virtue of the electronic stepping of the focus.

The only component of the X-ray diagnostic apparatus described above which has to be moved during examination is the collimator ring 30. This collimator ring is extremely simple to move because it is a lightweight component which is readily mounted. There are no electrical lines leading to this component so that there is no need for any particular cable guidance measures.

Figure 1B:
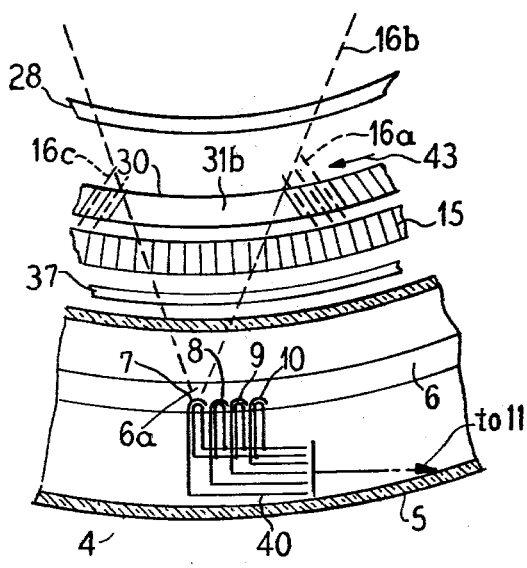
FIG. 1b is a view similar to FIG. 1a but illustrating the condition of the apparatus when one of the source regions of FIG. 1a is activated to produce an X-ray beam.

FIG. 1b is a view similar to FIG. 1a but showing the apparatus at a time when stepping switch 11 has been actuated to connect the negative terminal of high voltage rectifier 12 with conductor 40 of the set of conductors associated with the shifting of the X-ray beam 16b. With conductor 40 energized, cathode 7 emits an electron beam which impinges on anode 6 at the region 6a, FIG. 1b, to activate a focus region of anode 6 which is in alignment with cathode 7 as best as seen in FIG. 2.

Figure 2:
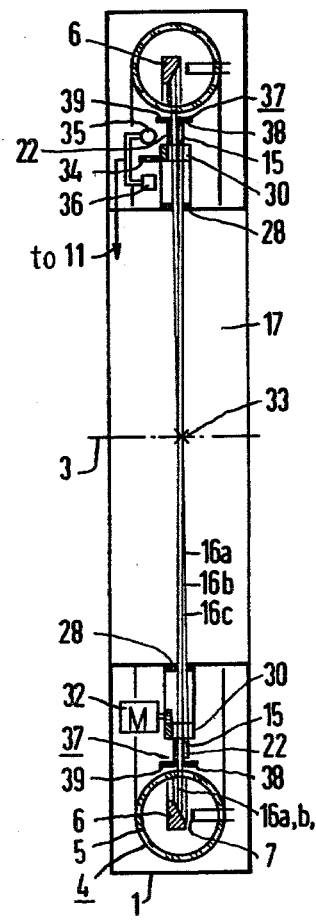
FIG. 2 is a somewhat diagrammatic longitudinal sectional view taken generally along the line II—II of FIG. 1.

The X-ray beam produced at the incremental focus region 6a of anode 6 passes through the gap between plates 38 and 39 of diaphragm 37, the plate 38, FIG. 2, serving to shield the adjacent detector region indicated at the lower part of FIG. 2, while diaphragm 37 and plate 28 delineate the beam so that it impinges upon the detector elements of detector 15 which are at the upper part of the detector ring as viewed in FIGS. 1 and 2.

By way of example, where collimator ring 30 is continuously driven during a scanning cycle, conductor 40 may be energized at the time when each collimator blade such as 30-1 in FIG. 1a approaches a leading margin of a given detector element such as 15-1. At this time transmitted rays in the bundle between rays 16c-1 and 16c-2 are impinging upon detector 15-1. The sample of transmitted radiation impinging on detector 15-1 as collimator blade 30-1 moves a distance equal to the blade separation then represents a sample of the transmitted radiation with respect to the given subject for a given angular relationship of the beam 16c to the subject. Successive samples may be taken in this way in response to successive pulses from the pulse generator 34–36 during the scanning cycle. The converter 20 may receive the output from pulse generator 34–36 and control the actual stepping of switch 11 as well as the sampling intervals for readout of the values from the series of detectors. Alternatively, as contemplated in FIG. 1, converter 20 can sequentially select the sets of three switches to be next actuated, for example in response to the respective preceding pulse from pulse generator 34–36, and the next following pulse from pulse generator 34–36, can then actually deactivate the previous set of switches and actuate the newly selected set of switches. Such sequential selection and actuation of switches in response to successive pulses is of course well known in the arts relating to digital circuits.

Referring to FIG. 1b, for clockwise rotation of collimator ring 30 as indicated by arrow 43, once the collimator ring had rotated through one angular increment corresponding to the separation between successive collimator plates, conductor 40 would be deenergized by stepping switch 11 and the similar conductor leading to the next succeeding cathode (to the left of cathode 7 as seen in FIG. 1b) would be energized to displace the fan shaped beam 16b to the next angular position. As previously stated, the sequential displacement of the beams may take place synchronously in steps in one degree.

It will be apparent that many modifications and variations may be effected without departing from the scope of the novel concepts of the present invention.

I claim as my invention:

1. An X-ray diagnostic apparatus for producing transverse layer images of a subject, comprising an X-ray measuring arrangement including an X-ray source for generating a fan-shaped X-ray beam which penetrates the subject, and a radiation receiver which determines the intensity of radiation behind the subject and has a series of detectors, and further comprising means for changing the direction of the X-ray beam, characterized in that the X-ray source comprises an annular anode arrangement with a series of anode regions, and a series of cathodes arranged adjacent the respective anode regions of the anode arrangement, means for switching on electron radiation in steps between at least one cathode and its adjacent anode region to successively change the direction of the X-ray beam, the anode arrangement and the radiation receiver being disposed in such a way that the X-ray beam initially passes laterally by the radiation receiver in the radiation direction and then impinges on respective detectors of the series after transmission through the subject, collimator means inwardly of the series of anode regions and arranged in such a manner that a wide fan-shaped X-ray beam is transmitted from an active anode region through the subject and in such a manner that the X-ray beam is collimated by the collimator means for impingement on respective detectors of the series, and means whereby said collimator means is operative in each successive direction of the X-ray beam for directing the radiation of the X-ray beam from the active anode regions to respective sets of detectors of said series, said radiation receiver having said series of detectors arranged inwardly of the anode regions of said annular anode arrangement so that the anode regions enclose the radiation receiver and the radiation receiver is closer to the subject than the annular anode arrangement.

2. An apparatus as claimed in claim 1, characterized in that all the cathodes are simultaneously connected to filament voltage and in that the switching means comprises a stepping switch device for successively connecting the negative terminal of a high-voltage source to the cathodes, the positive terminal of the high-voltage source being connected to the anode regions.

3. An apparatus as claimed in claim 1, characterized in that the means for switching on the electron radiation are designed in such a way that several X-ray beams penetrate the patient simultaneously from different directions and move in equal steps synchronously with one another.

4. An apparatus as claimed in claim 3, characterized in that three simultaneous X-ray beams are provided of which the central rays are staggered approximately 120°.

5. An X-ray diagnostic apparatus for producing transverse layer images of a subject, comprising an X-ray measuring arrangement including an X-ray source for generating a fan-shaped X-ray beam which penetrates the subject, and a radiation receiver which determines the intensity of radiation behind the subject and has a series of detectors, and further comprising means for changing the direction of the X-ray beam, characterized in that the X-ray source comprises an annular anode arrangement with a series of anode regions, and a series of cathodes arranged adjacent the respective anode regions of the anode arrangement, and means for switching on electron radiation in steps between at least one cathode and its adjacent anode region to successively change the direction of the X-ray beam, the anode arrangement and the radiation receiver being disposed in such a way that the X-ray beam initially passes laterally by the radiation receiver in the radiation direction and then impinges on respective detectors of the series after transmission through the subject, the radiation receiver having the series of detectors arranged in a ring inwardly of the annular anode arrangement, a collimator arranged inside of the radiation receiver and having blades aligned with a given anode region in each position of the collimator for directing transmitted radiation of the X-ray beam from the given anode region to respective detectors of said series, and having an opening for the passage of the X-ray beam from the given anode region and in the direction toward the subject under examination, and drive means for moving the collimator ring through successive positions synchronously with the change in the direction of the X-ray beam.

6. An X-ray diagnostic apparatus for producing transverse layer images of a subject, comprising an X-ray measuring arrangement including an X-ray source for generating a fan-shaped X-ray beam which penetrates the subject, and a radiation receiver which determines the intensity of radiation behind the subject and has a series of detectors, and further comprising means for changing the direction of the X-ray beam, characterized in that the X-ray source comprises an annular anode arrangement with a series of anode regions, and a series of cathodes arranged adjacent the respective anode regions of the anode arrangement, and means for switching on electron radiation in steps between at least one cathode and its adjacent anode region to successively change the direction of the X-ray beam, the anode arrangement and the radiation receiver being disposed in such a way that the X-ray beam initially passes laterally by the radiation receiver in the radiation direction and then impinges on respective detectors of the series after transmission through the subject, a collimator ring for directing the transmitted energy of the X-ray beam to a group of detectors of said series aligned therewith, means for rotating the collimator ring through successive angular positions to align successive anode regions with successive groups of detectors of said series; and said collimator ring having an opening for alignment with the active anode region for accommodating the passage of the incident energy of the beam from such active anode region toward the subject under examination, said radiation receiver having said series of detectors arranged inwardly of the anode regions of said annular anode arrangement so that the anode regions enclose the radiation receiver and the radiation receiver is closer to the subject than the annular anode arrangement.

7. An apparatus as claimed in claim 6 with said switching means having a pulse generator for controlling the operation thereof, said pulse generator being connected to the collimator ring to actuate the switching means in step with the rotation of the collimator ring.

8. An apparatus as claimed in claim 7, characterized in that the pulse generator comprises a cylindrical apertured ring with which an opto-electrical transducer is associated.

9. An apparatus as claimed in claim 8, characterized in that the radiation receiver is arranged laterally on an annular slit diaphragm (37) which comprises extensions (38, 39) perpendicularly of the layer plane for screening off the X-radiation directed at the subject under examination.

10. An apparatus as claimed in claim 1, characterized in that the radiation receiver (15) is in the form of a circular ring arranged laterally on an annular slit diaphragm (37) which comprises extensions (38, 39) perpendicularly of the layer plane for screening off stray radiation directed at the subject under examination and to direct the incident radiation of the beam laterally of the receiver while causing the transmitted radiation of the beam to impinge on a series of detectors of said receiver.

* * * * *